United States Patent [19]

Perrotta et al.

[11] 4,117,841

[45] Oct. 3, 1978

[54] MEDICATED BANDAGE POCKET

[76] Inventors: Anthony Perrotta; Charles Rollo, both of Box 81 Kensington Sta., Brooklyn, N.Y. 11218

[21] Appl. No.: 766,244

[22] Filed: Feb. 7, 1977

[51] Int. Cl.² .............................................. A61F 13/00
[52] U.S. Cl. .................................. 128/155; 128/268; 128/260
[58] Field of Search ............... 128/155, 156, 260, 268, 128/253

[56] References Cited

U.S. PATENT DOCUMENTS

| | | | |
|---|---|---|---|
| 2,489,675 | 11/1949 | Roberts | 128/268 |
| 2,595,606 | 5/1952 | Pohjola | 128/268 |
| 2,714,382 | 8/1955 | Alcala | 128/268 |
| 2,817,336 | 12/1957 | Kravitz et al. | 128/253 |
| 3,366,112 | 1/1968 | Antonik | 128/268 |

*Primary Examiner*—John D. Yasko
*Attorney, Agent, or Firm*—Robert D. Farkas

[57] ABSTRACT

A self-contained medicated bandage adhesive strip that has a rupturable pocket confining a quantity of suitable medicament and a self-contained means for rupturing the pocket.

6 Claims, 3 Drawing Figures

MEDICATED BANDAGE POCKET

BACKGROUND OF THE INVENTION

This invention relates to a self-contained, self-rupturable pocket having a medicament in combination with an adhesive bandage.

The prior art teaches a variety of bandages and bandages with medicament thereon, for example, as disclosed in U.S. Pat. Nos. 1,950,957; 3,297,032; 3,342,183; 3,366,112; 3,464,413; 3,565,075; 3,598,122; incorporated herein by reference; and others.

SUMMARY OF THE INVENTION

It is accordingly an object of the instant invention to provide for a new and improved medicating bandage.

It is another object to provide for one having the foregoing attributes wherein the medicament is maintained confined and impregnable until needed.

It is a further object to provide for the same at relatively little cost thereby making it generally available.

These and other objects and advantages of the invention will become more apparent from a consideration of the following detailed disclosure and claims and by reference to the accompanying drawings in which:

Figure 1:
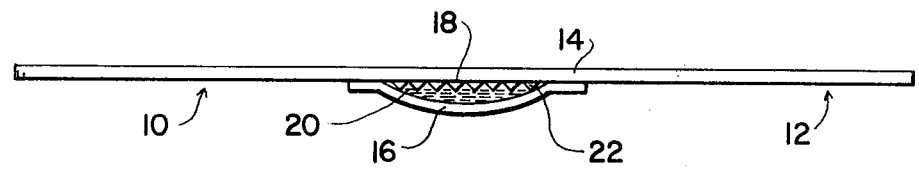
FIG. 1 is a side elevational view.
Figure 2:
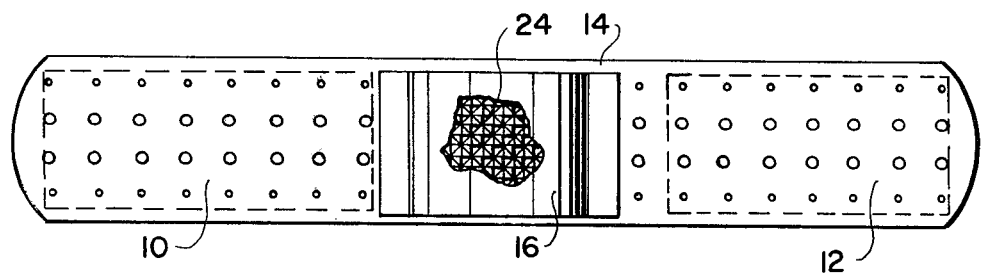
FIG. 2 is a plan view.
Figure 3:
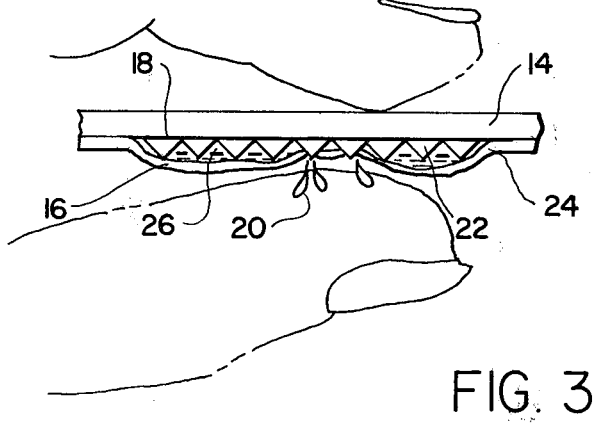
FIG. 3 is a perspective view of a portion of the bandage.

Broadly speaking, the instant invention includes the provision of a bandage adapted to releasably confine a quantity of active substance therefrom, comprising at least one adhesively coated bandage strip having two opposing surfaces, the adhesive being on one surface thereof, at least one partially rigid pointed member disposed on a portion of the one surface and facing downward away therefrom, a liquid impermeable sheet communicating with the one surface at opposing ends thereof and being spaced apart therebetween forming a cavity exposing the pointed members, a quantity of liquid or gell active substance disposed in the cavity and adapted to be released therefrom by forcibly puncturing the liquid impermeable sheet.

DETAILED DISCLOSURE

Referring more particularly to the drawings, there is shown a conventional adhesive bandage which includes a pair of opposing adhesively coated plastic strips 10, 12 with a gauze or plastic pad member 14 disposed therebetween or in the center of a single length of plastic strip. The adhesive is the conventional pressure sensitive adhesive customarily employed in bandages. If desired, the gauze portion 14 may be omitted and a length of liquid impermeable sheet 16, shorter than the strip 10 but approximately as wide is disposed along a portion thereof. Disposed between the sheet 16 and one surface 18 of the strip 10 is a quantity of a suitable liquid or gell 20 medicament, therapeutic, anesthetic, antiseptic or like substance. Also disposed against the undersurface 18 is at least one, preferably several, pointed members 22 that are sufficiently or partially rigid (i.e., plastic teeth) that the application of pressure against the sheet 16 causes the same to be brought in contact with the members 22 whereby it is punctured and the material 20 released therethrough onto the wound.

An alternative embodiment contemplates having member 16 constructed of a liquid permeable, preferably absorbent material (i.e., gauze) but having a liquid impermeable layer 24 disposed between it 16 and the liquid 20 in the cavity 26 formed between the same and the members 22. The members 22 in either embodiment, the members 22 are suitably affixed to the undersurface 18 such that the points thereof face downward towards the sheet 16 into the cavity 26.

Since it is obvious that numerous changes and modifications can be made in the above-described details without departing from the spirit and nature of the invention, it is to be understood that all such changes and modifications are included within the scope of the invention.

I claim:

1. A bandage adapted to releasably confine a quantity of active substance therefrom, comprising at least one adhesively coated bandage strip having two opposing surfaces, said adhesive being on one surface thereof, at least one partially rigid pointed member disposed on a portion of said one surface and facing downward away therefrom, a liquid impermeable sheet communicating with said one surface at opposing ends thereof and being spaced apart therebetween forming a cavity exposing said pointed members, said liquid impermeable sheet extending partially over said one surface of said adhesively coated strip, a quantity of liquid or gell active substance disposed in said cavity and adapted to be released therefrom by forcibly puncturing said liquid impermeable sheet.

2. The bandage as defined in claim 1 further including a sheet of liquid permeable material on the non-communicating surface of said liquid impermeable sheet.

3. The bandage as defined in claim 1 wherein said sheet and said strip are of substantially the same width.

4. The bandage as defined in claim 1 wherein there are two opposing strips with said liquid impermeable sheet disposed therebetween.

5. The bandage as defined in claim 1 wherein there are a plurality of said members, each being frusco-conical in shape.

6. The bandage as defined in claim 1 wherein said active substance is selected from the group consisting of medicinally, therapeutically, antimicrobially, and anesthetically active substances.

* * * * *